United States Patent
Bergström

[11] Patent Number: 6,070,584
[45] Date of Patent: Jun. 6, 2000

[54] SUPPORT STRUCTURE FOR FIXING A MEDICAL INSTRUMENT

[76] Inventor: Bo S Bergström, Kristinebergsgaten 11, S-792 34 Mora, Sweden

[21] Appl. No.: 09/051,965

[22] PCT Filed: Oct. 25, 1996

[86] PCT No.: PCT/SE96/01375

§ 371 Date: Apr. 24, 1998

§ 102(e) Date: Apr. 24, 1998

[87] PCT Pub. No.: WO97/15239

PCT Pub. Date: May 1, 1997

[30] Foreign Application Priority Data

Oct. 26, 1995 [SE] Sweden ................................ 9503796

[51] Int. Cl.[7] ........................................... A61B 15/00
[52] U.S. Cl. ........................................ 128/845; 248/316.4
[58] Field of Search ................................... 128/845, 846; 248/229, 231.4, 231.6, 216.16, 316.16, 316.4

[56] References Cited

U.S. PATENT DOCUMENTS 5,224,680  7/1993  Greenstein et al. .
5,351,676  10/1994  Putman .

FOREIGN PATENT DOCUMENTS

| 0 696 442 | 2/1996 | European Pat. Off. . |
| 30 21 194 | 12/1980 | Germany . |
| 2 180 754 | 4/1987 | United Kingdom . |
| WO 94/05215 | 3/1994 | WIPO . |

Primary Examiner—Michael A. Brown
Attorney, Agent, or Firm—Young & Thompson

[57] ABSTRACT

Support structure for fixing a laparoscope in a predetermined position relative to a patient on an operating table. The support structure comprises a vertical support arm which is displaceable on a horizontal support arm directed transversely to the operating table. The vertical support arm carries a slide body with a shelf for the laparoscope. The slide body has a friction member creating against the vertical support arm a friction selected so that the slide body is displaceable by hand force but retains its position when it is only loaded by the laparoscope.

5 Claims, 1 Drawing Sheet

SUPPORT STRUCTURE FOR FIXING A MEDICAL INSTRUMENT

FIELD OF THE INVENTION

The present invention relates to a support structure for fixing a medical instrument in a predetermined position, comprising at least one elongated support member having means for fixing the same in a predetermined position and being connected to a first support arm laterally directed from said support member, said first support arm being in turn connected to a second support arm forming an anise with said first support arm and supporting a slide body, which has means to carry said instrument and is displaceable and fixable relative to the second support arm, the support member and the interconnections of the support arms comprising means to permit lateral displacement of the second support arm relative to the support member.

BACKGROUND OF THE INVENTION

In laparoscopy, for example, a camera is usually coupled to the laparoscope. The operator moves the instrument and the laparoscope down through entrance ports, so-called trocars, placed in the abdominal wall. In order to enable the operator to use both hands, an assistant/cameraman is required to hold and guide the laparoscope/camera as the operator desires. Savings can be made if an operation assistant can be replaced by a mechanical structure which can hold the medical instrument, e.g. the laparoscope, in a predetermined position and which can be simply repositioned by the operator himself. Various devices are known which can be used for this purpose, but all are complicated by having motor-driven functions. Such a known device is shown and described in U.S. Pat. No. 5,351,676. Here there are achieved the functions described by way of introduction with the aid of telescoping or articulated arms with electric motors and electromagnetically controlled braking means for adjusting and fixing in a certain position. This known device is particularly expensive and complicated.

SUMMARY OF THE INVENTION

The purpose of the present invention is in general to achieve a support structure of the type described by way of introduction which consists of few parts, is simple and inexpensive, but still fulfills the requirements which are placed on its use, in particular in laparoscopy.

This is achieved according to the invention by virtue of the fact that the second support arm extends vertically from the laterally directed first support arm and that the slide body is displaceable on the second support arm against the effect of a friction which is selected so that the slide body is displaceable by hand force but retains its position when it is only loaded by the medical instrument.

BRIEF DESCRIPTION OF THE DRAWINGS

The invention will be described in more detail with reference to examples shown in the accompanying drawings, where.

DETAILED DESCRIPTION OF THE INVENTION

Figure 1:
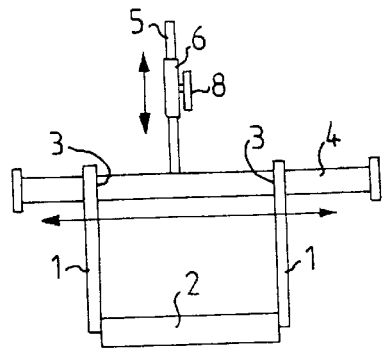
FIG. 1 shows a schematic front view.
Figure 2:
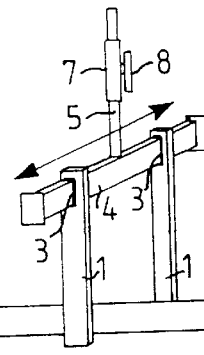
FIG. 2 shows a schematic view obliquely from the side.
Figure 3:
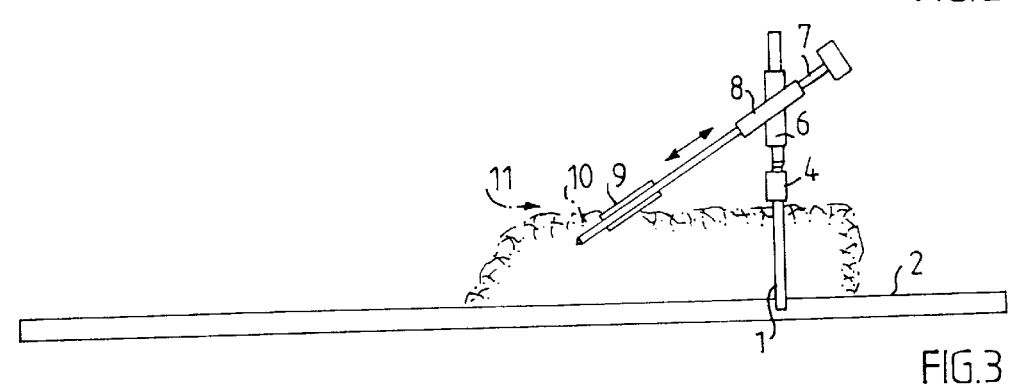
FIG. 3 shows a schematic side view of a first embodiment of a support structure according to the invention.

The support structure shown in FIGS. 1–3 comprises first structure members in the form of two posts 1, which are designed to be fixed vertically on either side of an operating-table 2, for example, with the aid of existing fixing means on the operating-table which are used to fix sedation equipment. The posts are provided at their upper ends with through-holes 3 of rectangular cross-section, through which a support arm 4 extends. The support arm 4 is of corresponding cross-section and extends with very little play through the holes 3, so that it can be displaced laterally by hand but is prevented from rotation.

On the support arm 4, a second support arm 5 is fixed in a position in which it extends vertically upwards from the support arm 4. The support arm 5 is of circular cross-section and extends through a tubular slide body 6, the inner surface of which is so adapted to the outer surface of the support arm 5 that it can be displaced upwards and downwards on the vertical support arm by hand against a certain resistance caused by friction.

The slide body 6 can have an elastic lining, for example, which provides grip between the slide body 6 and the support arm 5 so that the slide body retains its position when it is loaded by a medical instrument such as a laparoscope 7, which rests freely on a shelf 8 tippably joined to the slide body, which can be easily displaced by hand together with the laparoscope 7 upwards and downwards along the support arm.

FIG. 3 shows a laparoscope 7 which extends through a trocar 9, which is in place in the abdominal wall 10 of a patient 11 resting on the operating-table 2. The trocar 9 has a valve/rubber packing (not shown), through which the laparoscope 7 extends and which, due to friction, fixes the laparoscope axially. By displacing the horizontal support arm 4 horizontally relative to the posts 1 and by displacing the slide body 6 vertically relative to the support arm 5, the distal end of the laparoscope 7 can be directed to any selected position within the operating range. The frictional fixing of the laparoscope 7 in the rubber packing/valve of the trocar 9, in combination with sliding over the shelf, will mean that the distance of the laparoscope from the operating area 8 will remain unchanged.

Figure 4:
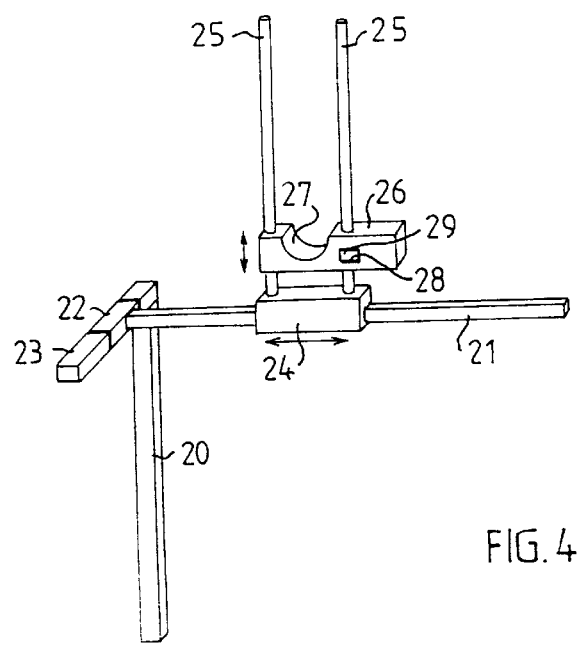
FIG. 4 shows a schematic perspective view of a second embodiment of a support structure according to the invention.

FIG. 4 shows a second embodiment of a support structure according to the invention. It has a single vertical post 20, intended to be fixed to one side of the operating-table, and a laterally directed support arm 21, which is fixed to a sleeve 22 which is displaceably mounted on an additional support arm 23 radially joined to the post 20. The post 20 is intended to be fixed relative to the operating-table 2 so that the arm 23 extends in the longitudinal direction of the table 2. The arm 23 and the sleeve 22 are of rectangular cross-section to prevent the sleeve from rotating relative to the arm. This makes the laterally directed support arm 21 displaceable in the longitudinal direction of the table at the same time as it is stabilized horizontally.

The support arm 21 is of rectangular cross-section and carries a sleeve 24 of corresponding cross-section, which is displaceable but non-rotatable relative to the arm 21. A pair of parallel rods 25 are fixed to the sleeve 24 and extend vertically upwards. The rods 25 extend through parallel bores in a slide body 26. which is provided with a depression 27 forming a shelf for a laparoscope. One of the bores in the slide body 26 is intersected by a rectangular cavity 28 in which there extends a rubber element 29 of complementary shape. The rubber element 29 has a bore through which the rod 25 extends in the associated bore in the slide body. The rubber element 29 accesses a friction element to fix the slide body in the set position relative to the rods 25 and it is easily replaced when worn.

I claim:

1. A support structure for fixing a medical instrument in a predetermined position, comprising:

at least one elongated support member extending in a first direction of a first axis;

an elongated first support arm coupled to said support member, said first support arm extending in a second direction of a second axis which extends at a first angle relative to said first axis;

at least one elongated second support arm coupled to said first support arm, said second support arm extending in a third direction of a third axis which extends at a second angle relative to said second axis, said second support arm being movable in said second direction;

a slide body friction fit to said second support arm, said slide body including means for carrying the medical instrument, and being movable in said third direction by hand force against said friction fit, but retaining its position when carrying the medical instrument.

2. The support structure according to claim 1, wherein said at least one support member comprises two support members.

3. The support structure according to claim 1, wherein said second support arm is fixed to said first support arm, and said first support arm is movable in said second direction.

4. The support structure according to claim 1, wherein said at least one elongated second support arm comprises two parallel second support arms, said slide body being friction fit to said two parallel second support arms.

5. The support structure according to claim 4, wherein said two parallel second support arms are attached to and extend through parallel bores in a sleeve, said sleeve being coupled to said first support arm and movable in said second direction, at least one of said bores containing a friction member.

* * * * *